US006810880B1

(12) United States Patent
Jennings, Jr. et al.

(10) Patent No.: US 6,810,880 B1
(45) Date of Patent: Nov. 2, 2004

(54) SURGICAL IMPLANT SYSTEM

(75) Inventors: Paul B. Jennings, Jr., Flagstaff, AZ (US); Paul D. Drumheller, Flagstaff, AZ (US); Terry A. Hubbard, Flagstaff, AZ (US); Krzysztof R. Pietrzak, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 09/546,549

(22) Filed: Apr. 10, 2000

(51) Int. Cl.[7] .............................................. A61B 19/00
(52) U.S. Cl. ...................................... 128/849; 128/852
(58) Field of Search ............................... 128/845–856; 604/317, 322, 356

(56) References Cited

U.S. PATENT DOCUMENTS

| | | | | |
|---|---|---|---|---|
| 4,649,572 A | * | 3/1987 | Roessler | 2/49 |
| 4,772,261 A | | 9/1988 | Von Hoff et al. | |
| 5,122,114 A | | 6/1992 | Miller et al. | |
| 5,217,443 A | * | 6/1993 | Oxley | 604/317 |
| 5,312,364 A | | 5/1994 | Jacobs | |
| 5,452,730 A | | 9/1995 | Cruz | 128/849 |
| 5,514,123 A | | 5/1996 | Adolf et al. | 604/411 |
| 5,596,814 A | | 1/1997 | Zingle et al. | |
| 5,730,530 A | * | 3/1998 | Stoddard | 383/113 |
| 5,772,644 A | * | 6/1998 | Bark | 604/317 |
| 5,876,855 A | | 3/1999 | Wong et al. | |
| 5,902,745 A | | 5/1999 | Butler et al. | |
| 5,913,998 A | | 6/1999 | Butler et al. | |
| 5,916,202 A | | 6/1999 | Haswell | 604/356 |
| 5,957,913 A | | 9/1999 | de la Torre et al. | 606/1 |
| 6,308,875 B1 | * | 10/2001 | Almo | 224/660 |

FOREIGN PATENT DOCUMENTS

WO    WO 94/15663    7/1994

OTHER PUBLICATIONS

Der Anaesthesist, Jun. 1989, vol. 38, No. 6, pp. 327–329.
Critical Care Medicine, Official Journal of the Society of Critical Care Medicine, Apr. 1991, vol. 19, No. 4, pp. 491–496.
Critical Care Medicine, Official Journal of the Society of Critical Care Medicine, May 1987, vol. 15, No. 5, pp. 499–502.
Intensive Care Medicine, 1984, vol. 10, No. 5, pp. 297–300.
Journal of Thoracic and Cardiovascular Surgery, Jul. 1983, vol. 86, No. 1, pp. 146–150.
The Canadian Anaesthetists' Society Journal, Jan. 1981, vol. 28, No. 1, pp. 86–88.

* cited by examiner

*Primary Examiner*—Michael Brown
(74) *Attorney, Agent, or Firm*—Eric J. Sheets

(57) ABSTRACT

A surgical system, including a sealable pouch or envelope with surgical implements in the envelope is disclosed. The envelope is formed by the folds in a membrane and includes adhesive on the envelope to adhere the envelope to the surgical site. The system may include a port in the membrane to communicate between the interior and exterior of the envelope. When used for implant surgery, the port helps to provide sterile access to the implant site and also helps to ensure that the implant site does not become contaminated. The adhesive helps to position the system to the patient, and placement of the surgical implements inside the envelope helps to ensure sterility of the implements. The envelope can be opened over the surgery site and adhered to the incision site on the patient, thereby forming a sterile field.

97 Claims, 7 Drawing Sheets

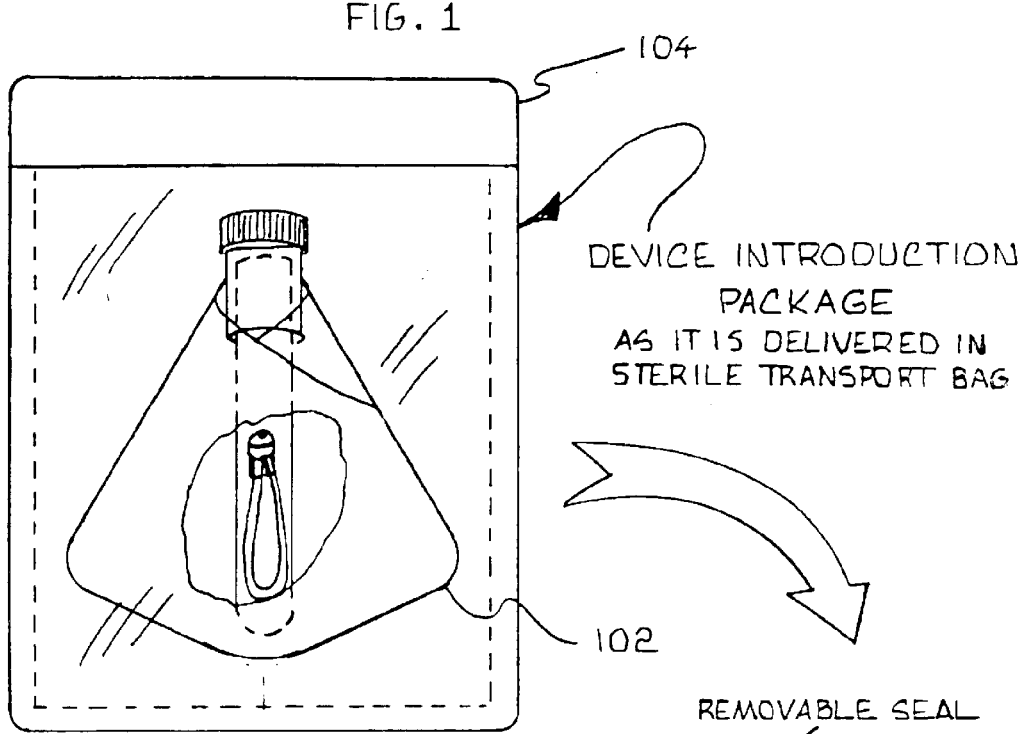
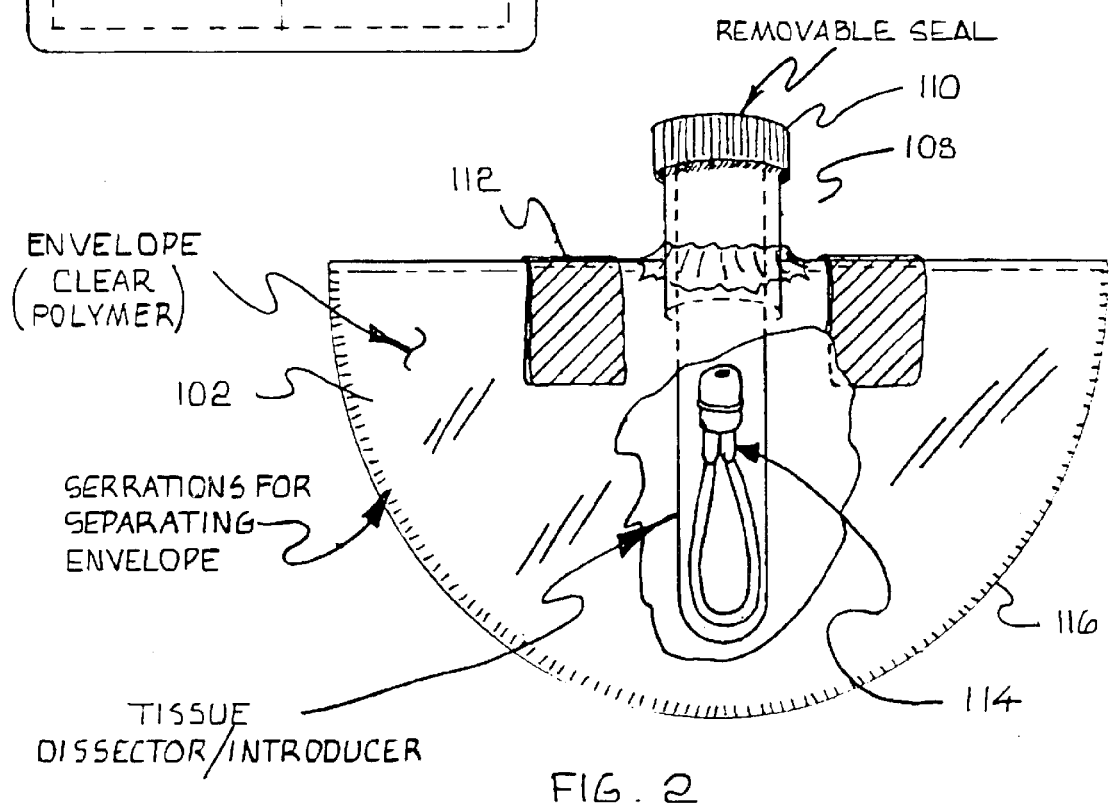

SURGICAL IMPLANT SYSTEM

BACKGROUND OF THE INVENTION

1. Field of the Invention

The invention relates to the field of surgery devices and methods, and more particularly to a system to provide and maintain a sterile surgical field, especially during implant surgery.

2. Background Information

Providing and maintaining sterile conditions during surgery is very important and the subject of many different apparatus, techniques and methods. Providing a sterile field is aided by thorough cleaning and disinfection or sterilization of the operating site. Contact disinfectants such as iodine scrub and alcohol are commonly known. Ultraviolet light is also known as a contact or surface disinfectant and is used in certain circumstances. Where complete disinfection or sterilization is not possible or practical, draping and shielding apparatus, techniques and methods are used. These include application of sterile cloth or plastic drapes over non-surgical areas of the patient and erection of shields between the surgical field and other areas of the operating room. Members of the operating team may use shields or respirators to reduce the probability of their introducing contamination into the field. Laminar flow ventilation systems in the operating theatre are also provided to sweep air-borne contaminants through and away from the patient before the contaminants have an opportunity to settle in the field. Of course, all the implements that are intended for use in the field are sterilized. Members of the surgical team also perform rigorous scrub and glove protocols to avoid contamination. All of these techniques are directed to providing and maintaining a sterile field for the surgery.

With all of these precautions, one source of contamination that is most difficult to control is contamination from the patient. Typically, this contamination is from organisms on the skin and particularly organisms on the skin at or in proximity to the incision site. Complete disinfection or sterilization of skin is almost impossible, as the required agents or techniques are very harsh or intolerable. Accordingly, the known techniques call for maximum draping or shielding in an attempt to prevent contaminant access from the patient's skin into the surgical field.

One draping technique calls for a skin scrub with the known surface disinfectants. Then, a flexible plastic drape or membrane is adhered to the patient over the projected incision site. The adhesive is either on the membrane before it is applied to the patient, or the adhesive is sprayed on the skin and the membrane is then adhered to the adhesive on the skin. The intent with this technique is to cover or shield as much of the skin as possible to prevent transmission of contaminants from the skin to the incision or wound. If the sterile membrane is properly applied, the surface that is exposed in the surgical field will be sterile. Then, during surgery, any fluids or implements that subsequently make contact with the membrane surface will remain sterile. If the fluids or implements are later introduced into the incision or wound, there is no contamination of the wound. This works well, except that surgery requires an incision and the incision must penetrate both the membrane and the skin. During this incision, there is localized bleeding and the blood readily picks up contaminants from the edge of the incised skin. Additionally, most of the adhesives used to adhere the membrane to the skin are not completely water tight and allow fluids, such as blood, to penetrate between the membrane and the skin. This intrusion of fluids further contaminates the fluids, producing additional possible contamination of the wound. The contaminated fluids then flow around the area of the incision and any instruments that make contact with the edges of the incision or the incision itself can become contaminated and carry the contamination deeper into the incision. The implements can also transfer the contamination to other implements that are in the field.

Infection and contamination during implant surgery is particularly problematic. For some surgical techniques, the time required to perform the implant is lengthy, providing greater opportunity for contamination. Additionally, immediately following the implant surgery, there may be an area of reduced vascularization in the area of the implant. This means that systemic treatments are less effective in treating infection. Where it might be appropriate to maintain a drain to treat infection with other deep surgical procedures, this may be inadvisable or impossible with an implant.

The methods available do not adequately address the problems of wound or incision contamination during implant operations. In particular, they do not address shielding or protection from the incision site itself. Systems and methods to address these and other deficiencies are needed.

SUMMARY OF THE INVENTION

In one embodiment, it is an object of the invention to provide a surgical system that includes a membrane to form a pouch or envelope, a seal to substantially close the envelope, and surgical implements in the envelope. The membrane includes an adhesive that is on the outside of the envelope to adhere to a surgical site and a fold in the membrane forms the envelope.

It is another object of the invention that the adhesive is on both sides of the envelope. It is another object of the invention that the adhesive is on only one side of the envelope. It is another object of the invention that the adhesive is applied to the patient and then the envelope is adhered to the patient.

It is another object of the invention that the system includes a sealed or sealable port with a port extension. It is another object of the invention that the port communicate between the interior and exterior of the envelope. It is another object of the invention that the port is sealed to the membrane. It is another object of the invention that the port is an area of the membrane that is intended to be incised.

It is another object of the invention that the port is near the fold in the membrane.

It is another object of the invention that the implement and the port are configured to cooperate with each other.

It is another object of the invention that there is an opener to open the envelope, the opener may be any of a number of different types, including a tear seal. It is another object of the invention that the opener allows the envelope to be substantially opened.

It is another object of the invention that when the envelope is opened, the membrane is substantially flat.

It is another object of the invention that the membrane is of many different types, including densified ePTFE, ePTFE, PTFE, plastic and cloth.

It is another object of the invention that the membrane is either flexible or rigid.

It is another object of the invention that the implements that are within the envelope of the system include surgical implements; implants; implant instruments; implant replacement instruments; implant power replacement instruments;

such as pacemaker power supplies; and surgical supplies, such as suture, gauze and sponges.

It is another object of the invention that the implements are disposable, reusable, plastic or durable.

It is another object of the invention that the system is made by forming an envelope in the membrane; disposing adhesive on the exterior of the envelope; placing surgical implements inside the envelope; and sealing the envelope.

It is another object of the invention that to use the system, an incision is made in the patient; the cover on the port is removed from the system; the port is inserted in the incision; adhesive is exposed on the membrane; and the membrane is adhered to the surgical site. It is another object of the invention that following the surgery, the port and membrane are removed and the incision is closed. It is another object of the invention that following the surgery, the port is removed, leaving the membrane adhered to the patient, and the incision is closed. It is another object of the invention that after the incision is closed, the membrane and adhesive are removed.

It is another object of the invention that the system and method of making and using the system provide a sterile surgical field with provision for reducing contamination of the surgical field, implant devices or implements. It is another object of the invention that for implant operations, the system is particularly advantageous in reducing the probability of infection in the vicinity of the implant.

The foregoing specific objects and advantages of the invention are illustrative of those which can be achieved by the present invention and are not intended to be exhaustive or limiting of the possible advantages that can be realized. Thus, the objects and advantages of this invention will be apparent from the description herein or can be learned from practicing the invention, both as embodied herein or as modified in view of any variations which may be apparent to those skilled in the art. Accordingly the present invention resides in the novel parts, constructions, arrangements, combinations and improvements herein shown and described.

BRIEF DESCRIPTION OF THE DRAWING

The foregoing features and other aspects of the invention are explained in the following description taken in conjunction with the accompanying figures wherein:

FIG. 1 illustrates an envelope according to one embodiment of the instant invention with packaging in a transport bag;

FIG. 2 illustrates an envelope according to one embodiment of the instant invention removed from the transport bag;

Figure 3:
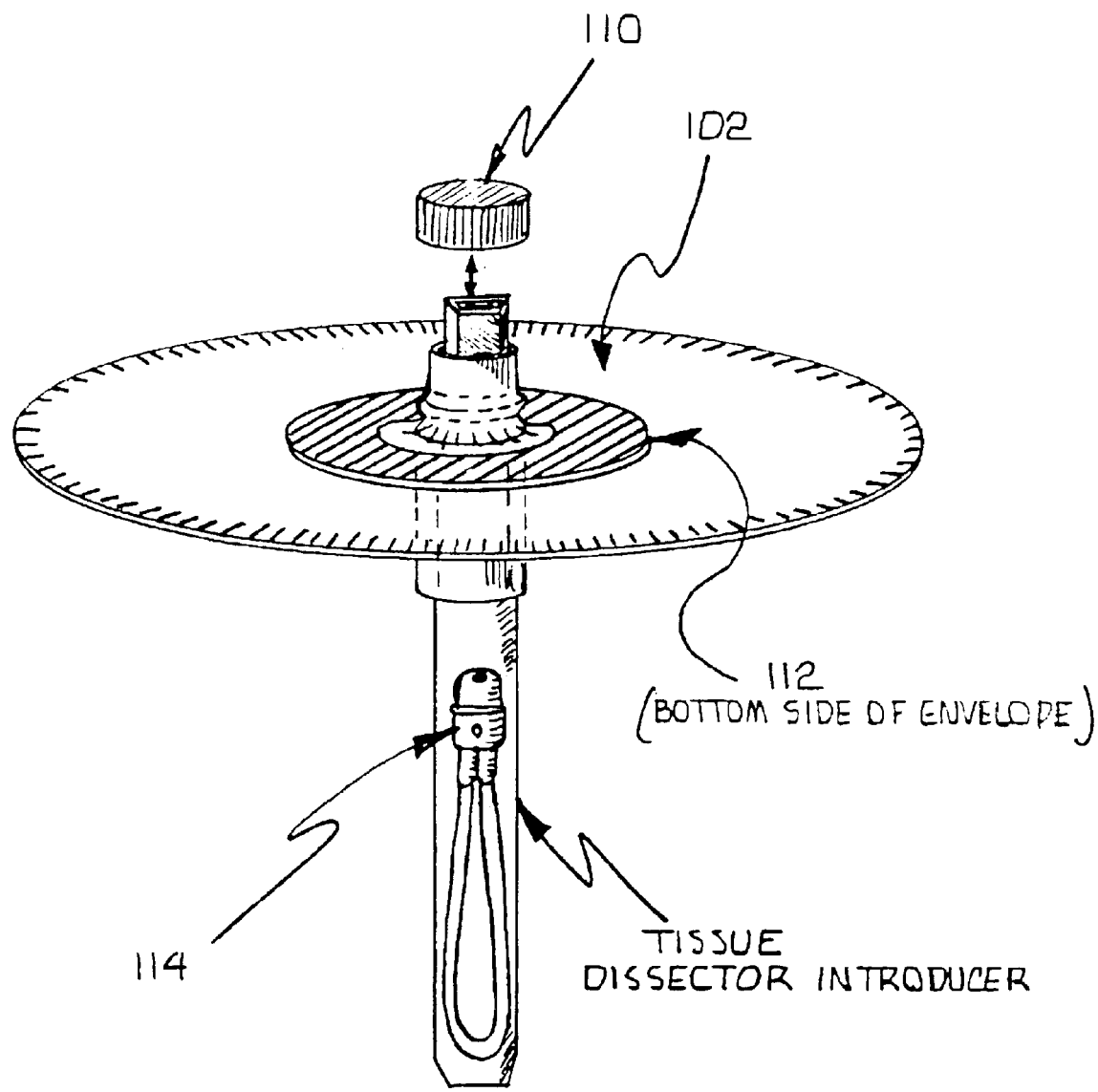
FIG. 3 illustrates an envelope according to one embodiment of the instant invention, as used during implant surgery.

It is understood that the drawings are for illustration only and are not limiting.

DETAILED DESCRIPTION OF THE INVENTION

The invention provides a surgical apparatus and system that is suitable for a number of surgical procedures. In one particular embodiment, the invention is suitable for implantation of certain apparatus or replacement of those apparatus. The instant invention is appropriate for surgical procedures involving patients with reduced or impaired immune systems, where infection or wound contamination presents an elevated risk. The instant invention is also appropriate for surgical procedures on otherwise normal patients.

There are numerous different implant systems, apparatus and devices. In the implantable containment apparatus that is described in U.S. Pat. No. 5,913,998, issued to Butler et al., ("the '998 patent") a tubular apparatus is subcutaneously implanted in a recipient by making a subcutaneous incision in the recipient, placing the containment apparatus in the recipient and closing the incision. The containment apparatus is typically implanted with an inert containment device or a containment device with angiogenic materials to facilitate vascularization. Within about one week, after the apparatus has vascularized in the recipient and the implant wound has started to heal, a second incision is made in the recipient near an access port of the containment apparatus. A cover on the access port is removed and the inert or angiogenic containment device is removed from the containment apparatus. Then, a containment device, such as the device disclosed in U.S. Pat. No. 5,902,745, issued to Butler et al. ("the '745 patent") is placed in the containment apparatus. This replacement containment device typically contains drugs or a cellular suspension in a cell rod. The cover on the access port of the containment apparatus is replaced and the second incision is closed. The containment apparatus and containment device may remain in the recipient for an indefinite period of time, or the containment device may require subsequent replacement. If there is a need for subsequent replacement of the containment device, an incision is again made near the access port of the containment apparatus. The cover on the access port is again removed and the containment device is replaced, followed by replacement of the cover and closure of the incision.

With every incision in the recipient, including the initial implantation of the containment apparatus and any placement or replacement of the containment device, there is a risk of wound infection. For recipients with normal immune systems this risk of infection does not pose a significant risk and can typically be handled with good surgical technique, plus topical or systemic antibiotics. For recipients with depressed immune systems, or allergies to antibiotics, an infection can have significant life threatening consequences. In addition, an infection at the site of the containment apparatus may require removal of the entire vascularized apparatus, resulting in even greater trauma and risk to the recipient. For these higher risk recipients, there is a need to reduce the probability of wound infection, by providing better sterile surgical procedures and apparatus. Of course, the advantages of the instantly described procedures and apparatus are also appropriate for other recipients.

As previously discussed, for many surgical procedures, skin contamination is a major contributor to infection, because skin is very difficult to completely disinfect or sterilize. Various techniques have been developed to reduce skin contact during surgery or shield skin in the surgical field. One surgical technique is a plastic sheet or membrane that is adhered over the patient's skin in the surgical field. This membrane or sheet is sometimes referred to as a drape or a dam. An incision is made directly through the membrane and the membrane helps to prevent blood and other fluids from making direct contact with exposed skin in the surgery field. However, any contamination in the region of the incision, and particularly where the membrane is incised, can be carried into the wound. Additionally, for implant procedures, and particularly apparatus implants as disclosed in the '998 patent, any contamination of the wound and implant is carried deep into the implant zone. This type of deep infection, which is problematic for most implants, is not readily treated with contact antibiotics. With a subcutaneous implant such as the '998 patent, due to the reduced vascularization in the implant zone, an infection is difficult to treat with systemic agents and may not be accessible to contact antibiotics. Thus, it is important for these types of implants that the implant itself remain free of contaminants during implantation. Avoidance of contact between the implant and the skin or incision site is very desirable. Additionally, avoidance of unnecessary contact between the implant and areas of the surgical field that may have become contaminated is desirable.

The containment apparatus of the '998 patent is typically implanted through a port or cannulae that is placed in a skin incision. Use of this type of port helps to prevent skin to implant contact and thereby reduces that source of possible infection. However, contamination of the surgical field remains a source of possible infection if the implant makes unintentional contact with contaminated objects in the surgical field prior to implant. Surgical techniques are intended to create and maintain a sterile surgical field. However, as implements are brought in and out of the field, contamination of the field can occur. If the field becomes contaminated, objects within the field will become contaminated as will the wound. There are many possible sources of contamination within the surgical field and the instant invention helps to reduce or eliminate the probability that the implantable containment apparatus or containment device makes unintended contact with any of these contaminants.

Fabrication of the Apparatus

In a preferred embodiment, illustrated in FIGS. 1 & 2, the invention includes a flat membrane 102, which is folded and sealed to form a pouch or envelope. The sealed envelope is packaged in a sterile transport bag 104 for handling and delivery to the surgical field. The membrane in this embodiment is a densified ePTFE and is thus flexible and readily takes a flat form in a surgical field. The membrane is circular and the fold 106 is approximately mid-point on the membrane, resulting in a half-circle envelope when folded. At approximately the mid-point of the fold, a port 108 is sealed into the envelope to create a passage from the interior of the envelope to the exterior of the envelope. When initially assembled, the port of the instant invention is sealed with a cap or cover 110. The cap or cover on the port helps maintain sterility in the interior of the sealed envelope. In the membrane area around the port, adhesive material 112 is placed on both sides of the envelope, generally surrounding the port 108. For ease of handling and use, this adhesive material is covered with a removable paper or plastic shield, to prevent unintended adhesive contact.

Before the envelope is sealed, various surgical implements 114 are positioned within the envelope. These implements include, but are not limited to, items such as implants, implant instruments, implant replacement instruments, batteries, and supplies. In a preferred embodiment, the implements in the envelope are an implantable containment apparatus with the associated surgical implant instruments or surgical replacement instruments. After positioning the surgical implements within the envelope, the envelope is sealed at the perimeter 116 by a technique that is suitable for the selected membrane. The sealing technique includes, but is not limited to, heat sealing, ultrasonic sealing, radio frequency induction sealing, adhesive sealing, and snap seals. As part of the seal there may be an integral opening device or opener, such as a tear-seal. After assembly, the apparatus is sterilized and sealed in a sterile transport bag 104.

Though a preferred embodiment includes a seal 110 on the port 108, there is no requirement that the port be sealed or covered. Additionally, a preferred embodiment includes a cover on the adhesive. However, there is no requirement that the adhesive be covered or shielded, or that the adhesive be applied to the membrane during assembly. The adhesive can be first applied to the recipient or patient and the membrane subsequently adhered to the adhesive.

If the membrane is flexible, it may accidentally adhere to the adhesive before the envelope is applied to the recipient. This could render the envelope useless. To avoid this condition, the adhesive portion can be made less flexible than the membrane SD that it is less likely to contact the membrane. Alternatively, as described above the adhesive is separate from the envelope. In this embodiment, a double stick adhesive is first adhered to the recipient and then the envelope is adhered to the adhesive. In this manner, if the double stick adhesive sheet is adhered to itself, it can be discarded without wasting the entire envelope and implements within the envelope.

A preferred embodiment of the material for the membrane or envelope is densified ePTFE. Densified ePTFE is made of PTFE and is similar to expanded or stretched ePTFE, but is different in that a PTFE shape is compressed through the application of heat and pressure while the shape itself is under a vacuum, thus forming the densified ePTFE article. The densified PTFE article exhibits increased flexural strength. U.S. Pat. No. 5,374,473 issued to Knox et al., the disclosure of which is incorporated herein by reference, discloses a technique for making densified ePTFE. Other materials for the envelope include: cellulose acetate; cellulose nitrate; polycarbonate; polypropylene; polyester; polyethersulfone; nylon; PVC; and polyvinylidene fluoride.

Sterilization is required after the implements are sealed in the envelope. Three common sterilization techniques include: steam autoclave, Ethylene Oxide (EtO) and radiation. With steam and EtO techniques, steam or chemical vapors must contact all surfaces of the envelope and the implements. If the sterilization technique uses steam or EtO and the membrane material is not otherwise sufficiently permeable to the gases, the envelope must include a permeable area. For example, the port cover can be made a permeable area. If the sterilization uses steam or EtO sterilization, the primary requirement is that there be sufficient permeability and size of the permeable area to allow for sterilization of the envelope and the contents.

Materials suitable for a permeable window area include: ePTFE, cellulose acetate, cellulose nitrate, polycarbonate, polypropylene, polyester, polyethersulfone, nylon, PVC, and polyvinylidene fluoride. It should be noted that if the envelope itself is formed of these or similar materials, there is no separate requirement for a gas permeable window area.

If radiation is used, the requirement for permeability of the envelope is eliminated. However, certain implements may not be compatible with radiation sterilization, requiring a steam or EtO technique.

Use of the Apparatus

Figure 4:
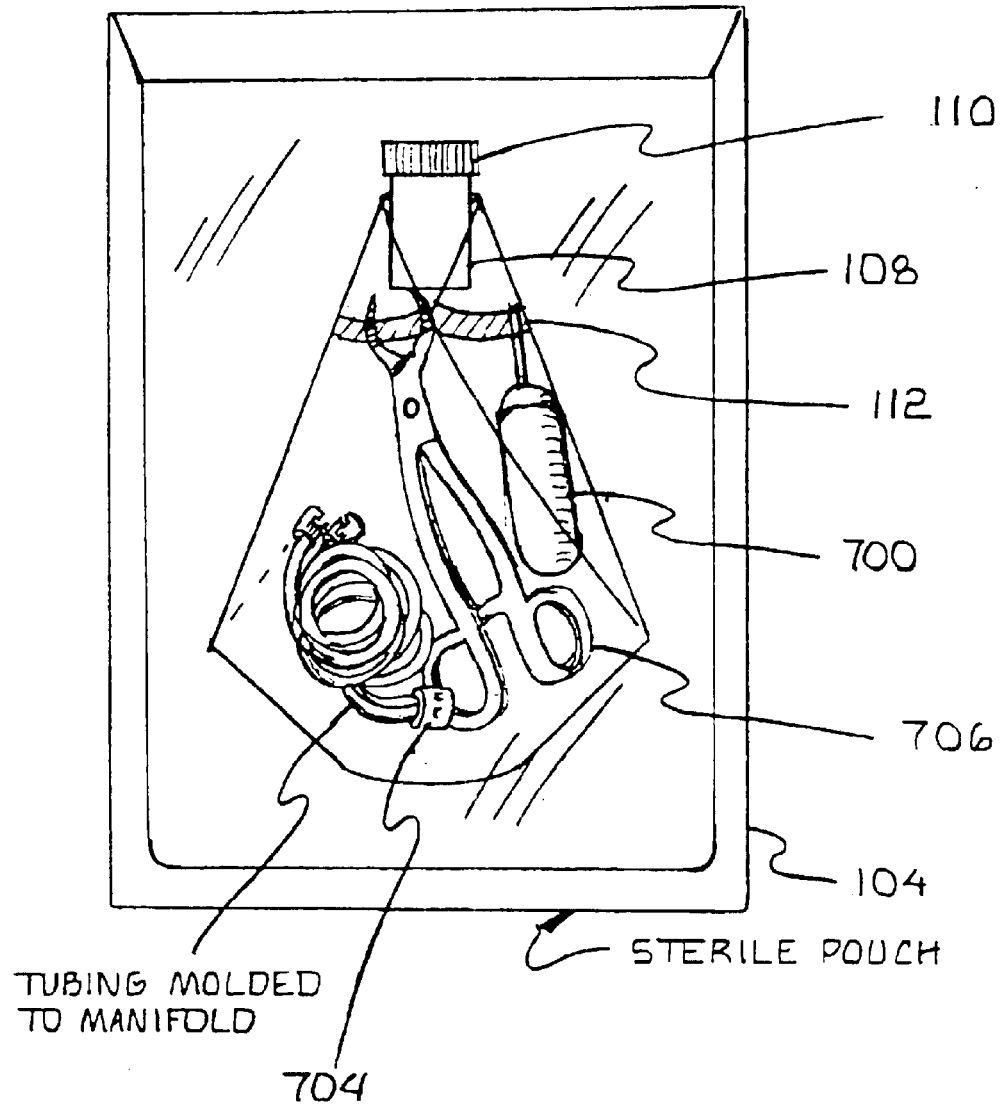
FIG. 4 illustrates an envelope packaged with surgical implements according to one embodiment of the instant invention.
Figure 5:
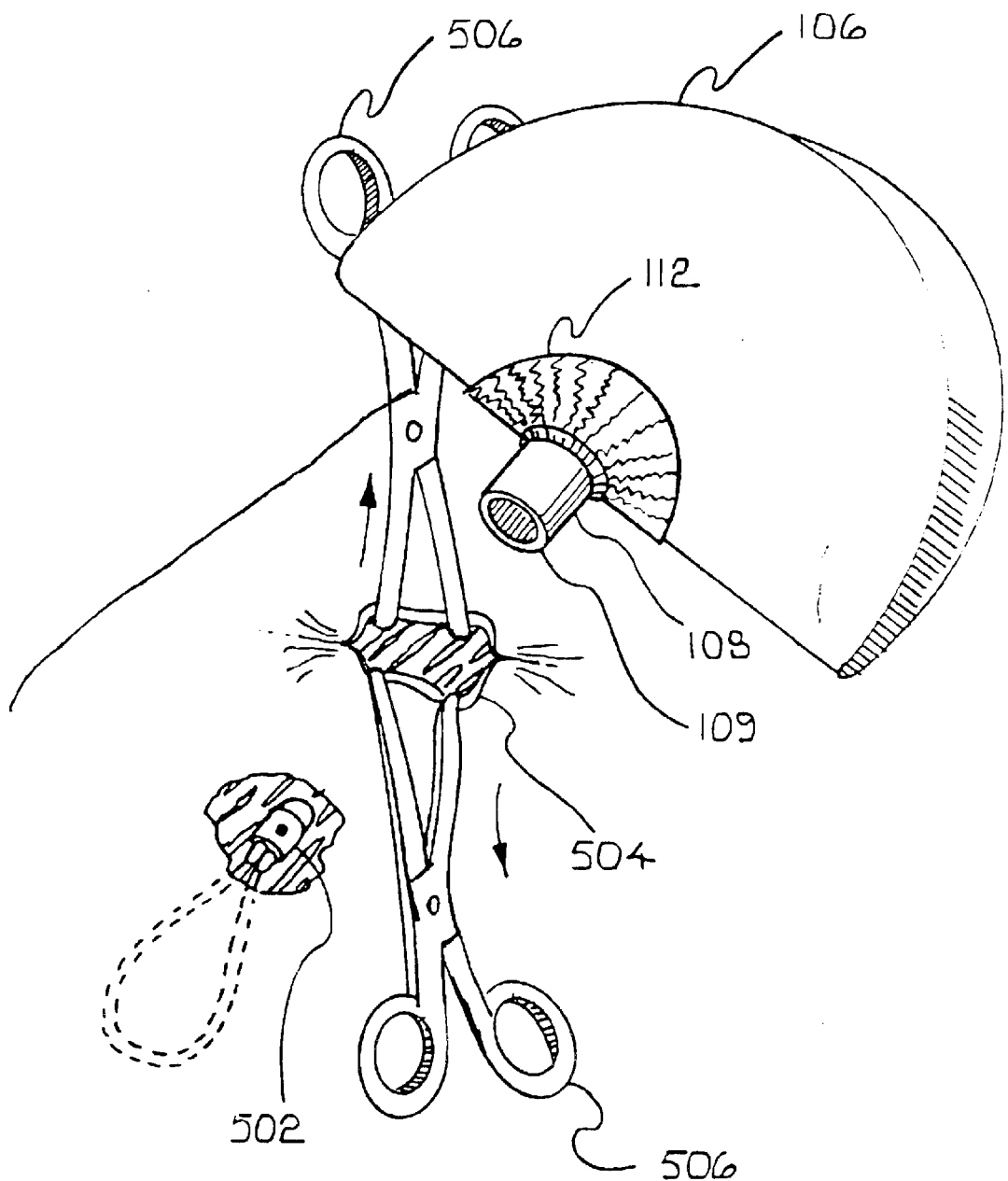
FIG. 5 illustrates an embodiment of the instant invention during implant replacement surgery.

The apparatus illustrated in FIG. 4 can be used to replace a cell rod (i.e., a containment device) in a previously implanted containment apparatus. The surgical site is prepared and disinfected by known techniques. As illustrated in FIG. 5, the multiple access port (MAP) 502 of the containment apparatus is palpated below the skin and an incision 504 is made between 2 and 4 cm from the MAP. The incision is made sufficiently large to allow the port 108 of the instant apparatus to pass. The instant invention is removed from the sterile transport bag and the seal 110 on the end of the port is removed. Using forceps 506, the edges of the incision 504 are separated to avoid contact between the incision and the port, and the port 108 of the instant invention is passed through the dermal layer and advanced toward the MAP 502 of the containment apparatus. As the port is passed through the incision, care is taken to avoid contact between skin at the exterior of the incision site and the port. This helps to avoid contamination of the sides of the port and dragging or introduction of that contamination into the wound. When the port is properly positioned in the incision, an end 109 of the extension on the port 108 is proximate the MAP 502. When properly positioned, the adhesive 112 that is between the envelope 106 and the recipient is exposed or positioned and the envelope is adhered to the surgical site. This has the effect of anchoring the envelope and port in position.

Figure 6:
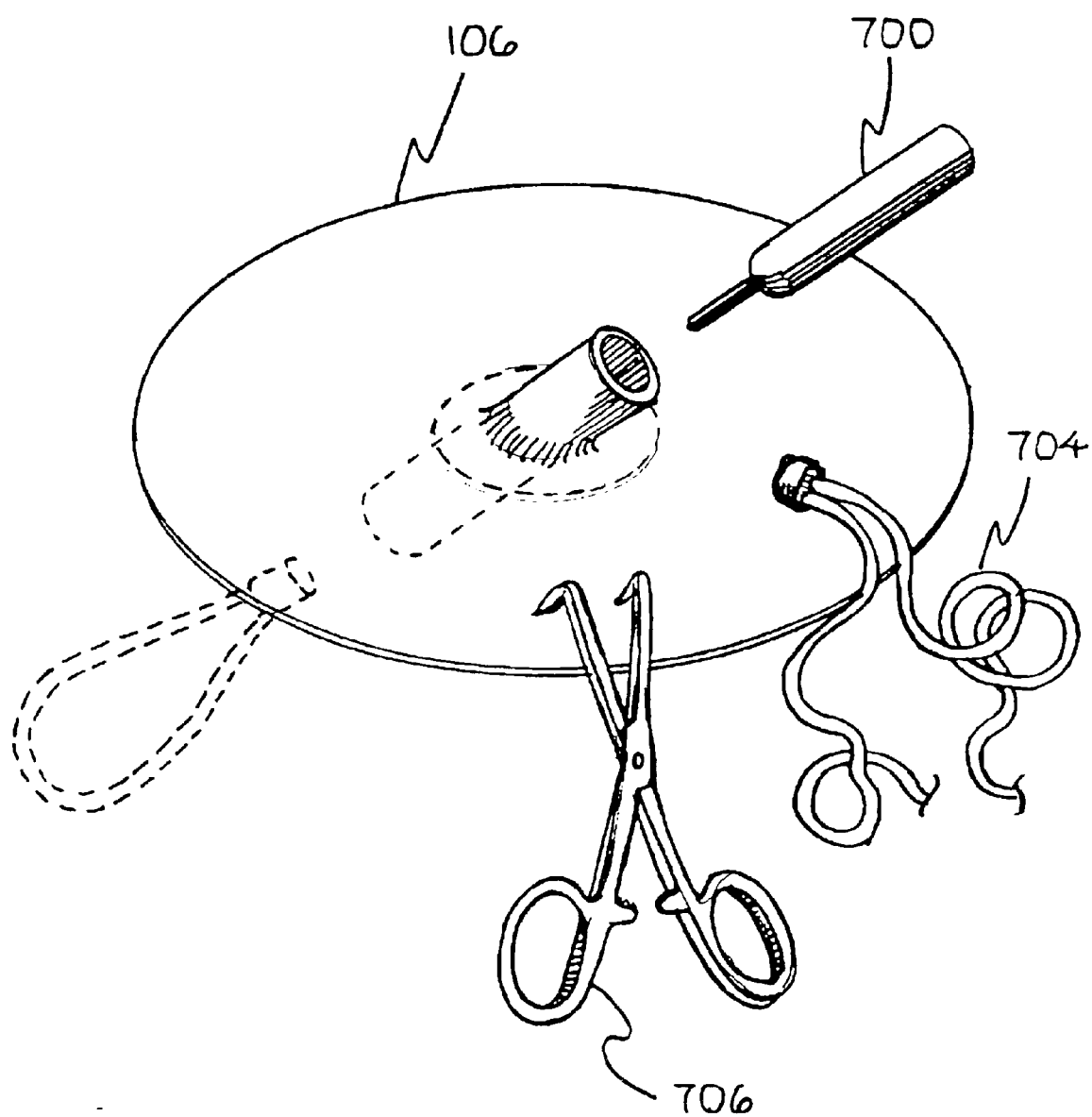
FIG. 6 illustrates an embodiment of the instant invention adhered to a patient during implant replacement surgery.

As illustrated in FIG. 6, after adhering the envelope 106 to the surgical site, the surgeon opens the envelope using any of a number of known techniques. These opening techniques include, but are not limited to pulling a tear strip, cutting the envelope with scissors, removing a peel strip, etc. Opening the envelope exposes the implements 700, 704, 706 inside the envelope. After opening the envelope, adhesive on the opposite side of the envelope is exposed or positioned and the envelope is then fully opened so that it can lay flat over the surgical site. The remainder of the adhesive on the membrane is then adhered to the surgical site. At this point, a new or fresh surgical field has been created by the combination of adhered and opened envelope and port. Additionally, all objects in the field were contained in the envelope, so they are sterile. With all required surgical implements contained within the envelope, there is no need to introduce additional implements into the field.

Figure 7:
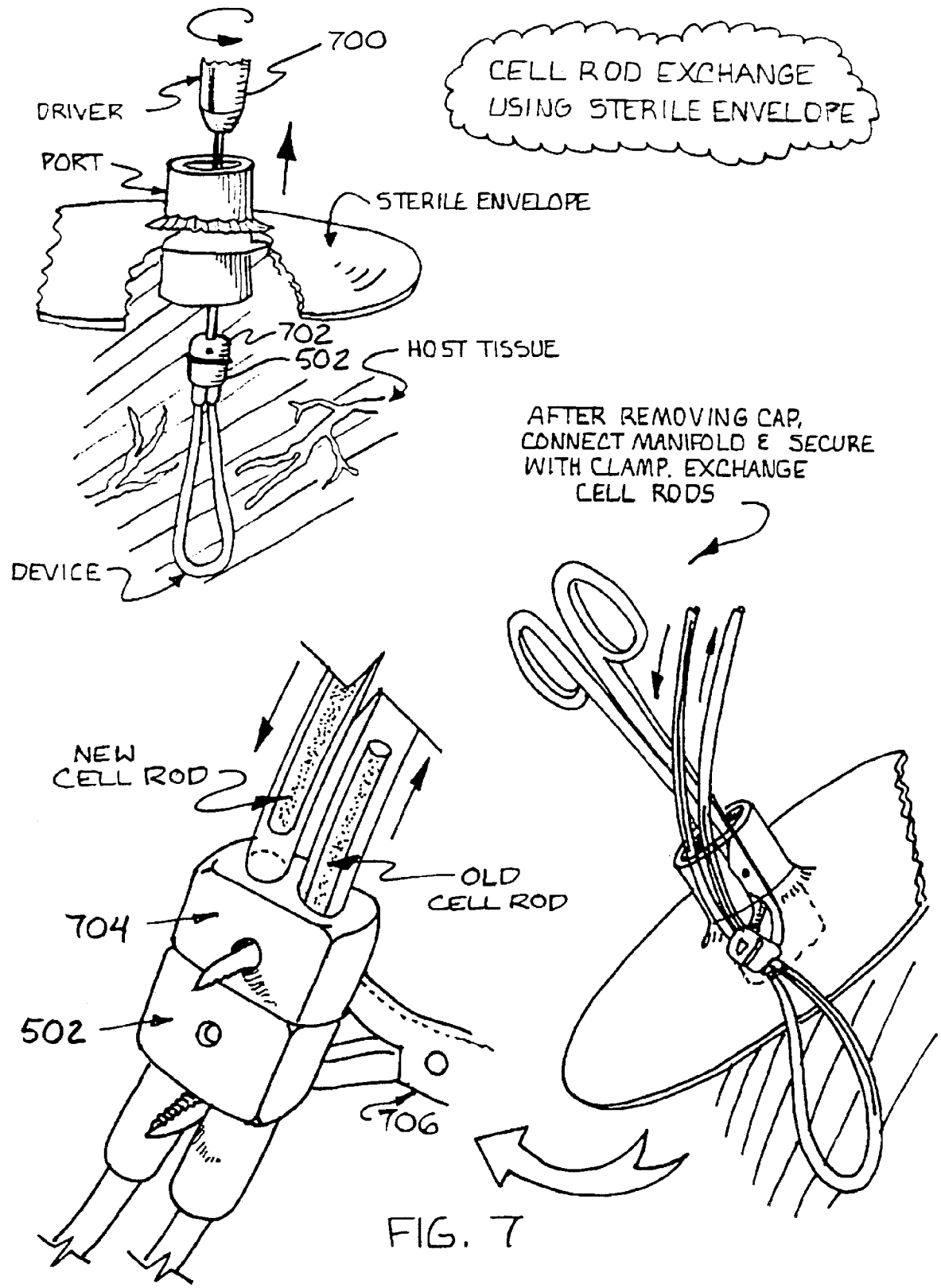
FIG. 7 illustrates an embodiment of the instant invention adhered to a patient during implant replacement surgery.

In the new or fresh surgery field, using the implements in the envelope, the tissue capsule surrounding the MAP is incised to expose a removable cover on the MAP. This incision is made using a scalpel or electro-cautery. Then, as illustrated in FIG. 7, using the screwdriver 700 in the envelope, the MAP cover 702 is removed. A manifold 704 is clamped to the MAP 502 using the manifold clamp 706. The manifold 704 and manifold clamp 706 are in the envelope. Using the manifold, the cell rod or containment device within the containment apparatus is removed. Removal is accomplished with a fluid stream, or by mechanically withdrawing the containment device from the apparatus. A replacement cell rod is then loaded into the containment apparatus from the manifold through the MAP using a fluid stream or mechanical insertion. After successful cell rod replacement, the manifold 704 and manifold clamp 706 are disconnected from the MAP 502. A new MAP cover, also in the envelope, is installed on the MAP using the screw driver 700. The MAP is repositioned inside the tissue cap and the port 108 is withdrawn from the incision. As the port is withdrawn, both the port and membrane are removed to expose the incision. The incision is now directly accessible, and suture or incision closure material, also within the envelope, is used to close the incision. Using known surgical incision closure techniques, the incision is closed. After the incision is closed, any adhesive that remains on the patient is removed.

Figure 8:
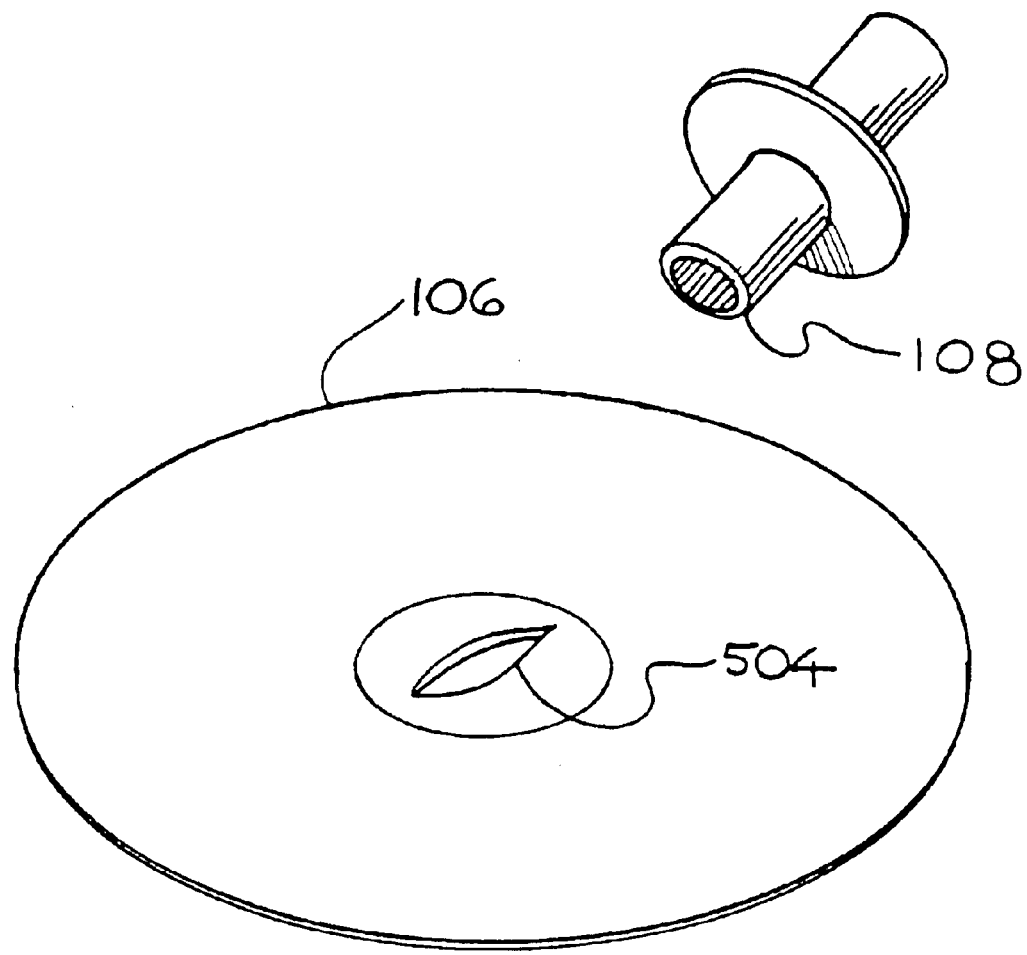
FIG. 8 illustrates an embodiment of the instant invention with the membrane adhered to a patient and the port removed to expose the incision.

In another embodiment, illustrated in FIG. 8, after the cell rod is replaced and the MAP repositioned in the tissue capsule, the port 108 is separated from the membrane 106 at a tear region, leaving the membrane 106 adhered to the surgical site. The incision 504 is now directly accessible and suture or incision closure material, also within the envelope, is used to close the incision. After the incision is closed, the membrane 106 is removed from the patient and any adhesive that remains on the patient is removed.

In a preferred embodiment, after the operation, the envelope, port and all used or unused implements within the envelope are discarded. However, it may be appropriate to recondition or reuse certain implements.

In a preferred embodiment, all implements required for the operation are within the envelope. However, it may be appropriate to have some implements in other sterile containers.

In a preferred embodiment, the port is sealed to the membrane. In another embodiment, the "port" may be merely an area of the membrane that is intended to be incised. Therefore, the port is not open until the membrane is incised. In this embodiment, the positioning of the implements within the envelope, adhering the envelope to the surgical site and then opening the envelope to form a barrier, drape or dam, before making the incision through the membrane helps to ensure a more sterile field.

In a preferred embodiment, the port has an extension to provide deep tissue access, such as to an embedded MAP. In another embodiment, there is no port extension and the port primarily provides a barrier between the exterior skin and the interior tissues.

In a preferred embodiment a cell rod is removed in one step and in a second step, a cell rod replaced. In another embodiment, the cell rods are exchanged at the same time.

The apparatus and method of the instant invention are suitable for access and removal of lesions or devices located subcutaneously or accessible via skin incisions. Examples include: tumors or other lesions located in muscle, fascia or bone; craniotomy surgical approaches; access to buried cardiac pacemaker components, and other buried devices; access to colostomy stomas; access to orthopedic appliances or to repair orthopedic abnormalities; in conjunction with intraosseus infusion devices; in conjunction with implantable therapy systems and methods; insertion/removal of peritoneal dialysis catheters; access to the lower GI tract and urogenital tract; ophthalmic surgery; laparoscopic procedures of the thorax, abdomen and joints; and other related procedures.

Although illustrative embodiments have been described herein in detail, it should be noted and will be appreciated by those skilled in the art that numerous variations may be made within the scope of this invention without departing from the principle of this invention and without sacrificing its chief advantages.

Unless otherwise specifically stated, the terms and expressions have been used herein as terms of description and not terms of limitation. There is no intention to use the terms or expressions to exclude any equivalents of features shown and described or portions thereof and this invention should be defined in accordance with the claims that follow.

We claim:

1. A surgical system comprising:
   a membrane the membrane further comprising:
      an adhesive disposed on a first side of the membrane to adhere to a surgical site; and
      a fold in the membrane to form an envelope, the first side of the membrane forming
   the exterior of the envelope;
      a seal to substantially close the envelope;
      an implement disposed within the envelope; and
      wherein the envelope is two sided as a consequence of the fold and the adhesive is disposed on both sides of the envelope.

2. A system according to claim 1, further comprising a removable cover on the adhesive.

3. A system according to claim 1, wherein the adhesive is disposed in the vicinity of the fold.

4. A system according to claim 1, further comprising a port communicating between the interior and the exterior of the envelope, wherein the port includes an extension for introduction into an incision.

5. A system according to claim 4, wherein the port includes a removable seal.

6. A system according to claim 4, wherein the port includes a seal cooperating with the membrane.

7. A system according to claim 4, wherein the port includes an opening in the membrane.

8. A system according to claim 4, wherein the port includes an area of the membrane intended for an incision.

9. A system according to claim 4, wherein the fold is proximate to the port.

10. A system according to claim 4, wherein the implement and port are configured to cooperate with each other.

11. A system according to claim 1 further comprising an opener to open the envelope.

12. A system according to claim 11, wherein the opener is configured to allow the envelope to be substantially opened.

13. A system according to claim 11, wherein the opener is configured to allow the membrane to be substantially flat.

14. A system according to claim 11, wherein the opener includes a tear seal.

15. A system according to claim 11, wherein the opener opens the seal.

16. A system according to claim 1, wherein the membrane is selected from the group that includes densified ePTFE, ePTFE, plastic and cloth.

17. A system according to claim 1, wherein the membrane is flexible or rigid.

18. A system according to claim 1 wherein the implement is selected from the group that includes implants, implant instruments; implant replacement instruments; implant power replacement instruments; and supplies.

19. A system according to claim 1, wherein the implement is disposable.

20. A system according to claim 1, wherein the implement is reusable.

21. A system according to claim 1, wherein the implement includes plastic parts.

22. A system according to claim 1, wherein the implement includes durable parts.

23. A system according to claim 22, further comprising a removable cover on the adhesive.

24. A system according to claim 22, wherein the adhesive is disposed in the vicinity of the fold.

25. A system according to claim 22, further comprising a port communicating between an interior and the exterior of the envelope.

26. A system according to claim 25, wherein the port includes a removable seal.

27. A system according to claim 25, wherein the port includes an extension for introduction into an incision.

28. A system according to claim 25, wherein the port includes a seal cooperating with the membrane.

29. A system according to claim 25, wherein the port includes an opening in the membrane.

30. A system according to claim 25, wherein the port includes an area of the membrane intended for an incision.

31. A system according to claim 25, wherein the fold is proximate to the port.

32. A system according to claim 25, wherein the port is configured to cooperate with a surgical implement.

33. A system according to claim 22, further comprising an opener to open the envelope.

34. A system according to claim 33, wherein the opener is configured to allow the envelope to be substantially opened.

35. A system according to claim 33, wherein the opener is configured to allow the membrane to be substantially flat.

36. A system according to claim 33, wherein the opener includes a tear seal.

37. A system according to claim 33, wherein the opener opens the seal.

38. A system according to claim 22, wherein the membrane is selected from the group that includes densified ePTFE, ePTFE, plastic and cloth.

39. A system according to claim 22, wherein the membrane is flexible or rigid.

40. A system according to claim 22, further comprising a surgical implement within the envelope.

41. A system according to claim 40, wherein the implement is selected from the group that includes implants, implant instruments; implant replacement instruments; implant power replacement instruments: and supplies.

42. A system according to claim 40, wherein the implement is disposable.

43. A system according to claim 40, wherein the implement is reusable.

44. A system according to claim 40, wherein the implement includes plastic parts.

45. A system according to claim 40, wherein the implement includes durable parts.

46. A surgical system comprising:
    a membrane, the membrane further comprising:
       an adhesive disposed on a first side of the membrane to adhere to a surgical site;
       a fold in the membrane to form an envelope, the first side of the membrane forming
    the exterior of the envelope;
    a seal to substantially close the envelope, and
       wherein the envelope is two sided as a consequence of the fold and the adhesive is disposed on both sides of the envelope.

47. A surgical system comprising:
    a membrane, the membrane including a fold to form an envelope, a first side of the membrane forming the exterior of the envelope;
    an area of the membrane configured to provide an opening in the membrane;
    a seal to substantially close the envelope; and
    a port disposed proximate to the fold and communicating between the interior and the exterior of the envelope, the port including an extension for insertion into an incision.

48. A system according to claim 47, further comprising adhesive cooperating with the membrane.

49. A system according to claim 48, further comprising a removable cover on the adhesive.

50. A system according to claim 48, wherein the adhesive is disposed in the vicinity of the fold.

51. A system according to claim 48, wherein the envelope is two sided as a consequence of the fold and the adhesive is disposed on both sides of the envelope.

52. A system according to claim 47, wherein the port includes a removable seal.

53. A system according to claim 47, wherein the port includes a seal cooperating with the membrane.

54. A system according to claim 47, wherein the port includes an opening in the membrane.

55. A system according to claim 47, further comprising a surgical implement within the envelope.

56. A system according to claim 55, wherein the implement and port are configured to cooperate with each other.

57. A system according to claim 55, wherein the implement is selected from the group that includes implants, implant instruments; implant replacement instruments; implant power replacement instruments; and supplies.

58. A system according to claim 55, wherein the implement is disposable.

59. A system according to claim 55, wherein the implement is reusable.

60. A system according to claim 55, wherein the implement includes plastic parts.

61. A system according to claim 55, wherein the implement includes durable parts.

62. A system according to claim 47, further comprising an opener to open the envelope.

63. A system according to claim 62, wherein the opener is configured to allow the envelope to be substantially opened.

64. A system according to claim 62, wherein the opener is configured to allow the membrane to be substantially flat.

65. A system according to claim 62, wherein the opener includes a tear seal.

66. A system according to claim 62, wherein the opener opens the seal.

67. A system according to claim 47, wherein the membrane is selected from the group that includes densified ePTFE, ePTFE, plastic and cloth.

68. A system according to claim 47, wherein the membrane is flexible or rigid.

69. A surgical system comprising:
a liquid water impermeable membrane configured to cover an incision site;
a medical grade adhesive disposed on a first side of the membrane to adhere the membrane to skin surrounding the incision site;
a port communicating between the first side of the membrane and a second side of the membrane, wherein the port is configured to permit a medical device to pass therebetween;
a removable microbe-impermeable seal attached to the port, and an extension on the port for placement in an incision.

70. The surgical system of claim 69, further comprising a fold in the membrane to form an envelope, wherein the first side of the membrane forms an exterior surface of the envelope, and a surgical instrument or medical device disposed within the envelope.

71. The surgical system of claim 70, further comprising a seal in the envelope.

72. The surgical system of claim 71, further comprising an opener for the seal.

73. A system according to claim 69, wherein the medical device is a cell containment device.

74. A system according to claim 69, wherein the medical device is a containment apparatus for a cell containment device.

75. The surgical system of claim 69, further comprising a removable cover on the adhesive.

76. The surgical system of claim 69, wherein the membrane includes a medical grade polymeric material.

77. The surgical system of claim 76, wherein the polymeric material is selected from the group that includes densified ePTFE, ePTFE, plastic and cloth.

78. A method to manufacture a surgical apparatus comprising:
forming an envelope with a membrane, the envelope configured to hold a surgical implement;
disposing an adhesive on an exterior of the envelope, the adhesive to adhere to a surgical site;
placing surgical implements in the envelope; and
sealing the envelope.

79. A method according to claim 78, further comprising disposing a removable cover on the adhesive.

80. A method according to claim 78, further comprising sterilizing the apparatus.

81. A method to manufacture a surgical apparatus comprising:
forming an envelope with a membrane, the envelope configured to hold 9 surgical implement, the membrane configured with a seal region to seal the envelope; and
disposing an adhesive on an exterior of the envelope, the adhesive to adhere to a surgical site.

82. A method according to claim 81, further comprising placing a surgical implement into the envelope.

83. A method according to claim 81, further comprising sealing the envelope.

84. A method according to claim 81, further comprising disposing a removable cover on the adhesive.

85. A method according to claim 81, further comprising sterilizing the apparatus.

86. A method to manufacture a surgical apparatus comprising:
placing surgical implements in an envelope that is formed with a membrane, the membrane including an adhesive disposed on an exterior of the envelope to adhere to a surgical site; and
sealing the envelope.

87. A method according to claim 86, further comprising disposing a removable cover on the adhesive.

88. A method according to claim 86, further comprising sterilizing the apparatus.

89. A method to manufacture a surgical apparatus comprising:
providing a liquid water impermeable membrane;
disposing a medical grade adhesive on a first side of the membrane the adhesive to adhere the membrane to skin surrounding an incision site;
configuring a port in the membrane, the port communicating between the first side of the membrane and a second side of the membrane, wherein the port is configured to permit a medical device to pass therethrough; and
configuring a removable microbe-impermeable seal attached to the port.

90. A method according to claim 89, further comprising creating an envelope by folding the membrane, wherein the first side forms an exterior of the envelope.

91. A method according to claim 90, further comprising sealing the envelope.

92. A method according to claim 90, further comprising disposing a surgical instrument within the envelope.

93. A method according to claim 90, further comprising disposing a medical device within the envelope.

94. A method according to claim 93, wherein the medical device is a cell containment device.

95. A method according to claim 93, wherein the medical device is a containment apparatus for a cell containment device.

96. A method according to claim 89, further comprising disposing a removable cover on the adhesive.

97. A method according to claim 89, further comprising sterilizing the apparatus.

* * * * *